United States Patent
Robert et al.

(10) Patent No.: US 8,569,289 B2
(45) Date of Patent: Oct. 29, 2013

(54) FUMARATE SALT OF 4-BROMOPHENYL 1,4-DIAZABICYCLO[3.2.2]NONANE-4-CARBOXYLATE, CRYSTALLINE FORMS THEREOF, PREPARATION THEREOF AND THERAPEUTIC USE THEREOF

(75) Inventors: Benoit Robert, Paris (FR); Laurent Salle, Paris (FR)

(73) Assignee: Sanofi, Paris (FR)

( * ) Notice: Subject to any disclaimer, the term of this patent is extended or adjusted under 35 U.S.C. 154(b) by 294 days.

(21) Appl. No.: 12/958,016

(22) Filed: Dec. 1, 2010

(65) Prior Publication Data

US 2011/0130389 A1   Jun. 2, 2011

Related U.S. Application Data

(63) Continuation of application No. PCT/FR2009/051039, filed on Jun. 2, 2009.

(30) Foreign Application Priority Data

Jun. 2, 2008   (FR) ..................... 08 02995

(51) Int. Cl.
*A61P 25/00*     (2006.01)
*A61P 25/18*     (2006.01)
*A61P 25/28*     (2006.01)
*A61K 31/551*    (2006.01)
*C07D 211/58*    (2006.01)
*C07D 243/08*    (2006.01)
*C07D 471/08*    (2006.01)

(52) U.S. Cl.
USPC ........................... 514/221; 540/556

(58) Field of Classification Search
USPC ........................... 514/221; 540/556
See application file for complete search history.

(56) References Cited

U.S. PATENT DOCUMENTS 6,987,106 B1   1/2006   Gallet et al.
2002/0177591 A1*  11/2002   O'Donnell et al. ........... 514/221
2007/0270373 A1   11/2007   Rieger et al.

FOREIGN PATENT DOCUMENTS

EP      1 231 212 A1     8/2002
WO      WO 00/58311     10/2000
WO      WO 2007/093600 A1   8/2007

OTHER PUBLICATIONS

Pichat et al, SSR180711, a Novel Selective alpha7 Nicotinic Receptor Partial Agonist: (II) Efficacy in Experimental Models Predictive of Activity Against Cognitive Symptoms of Schizophrenia, Neuropsychopharmacology (2007) 32 pp. 17-34.
Gould, Salt selection for basic drugs, Int'l J Pharmaceutics, (1986) 33 pp. 201-217.
International Search Report for WO2009/156678 dated Dec. 30, 2009.

* cited by examiner

*Primary Examiner* — Brenda Coleman
(74) *Attorney, Agent, or Firm* — Kelly L. Bender

(57) ABSTRACT

Fumarate salt of 4-bromophenyl 1,4-diazabicyclo[3.2.2] nonane-4-carboxylate, crystalline forms thereof, methods of preparation thereof, and therapeutic use thereof.

15 Claims, No Drawings

FUMARATE SALT OF 4-BROMOPHENYL 1,4-DIAZABICYCLO[3.2.2]NONANE-4-CARBOXYLATE, CRYSTALLINE FORMS THEREOF, PREPARATION THEREOF AND THERAPEUTIC USE THEREOF

This application is a continuation of International Application No. PCT/FR2009/051039, filed Jun. 2, 2009, which is incorporated herein by reference in its entirety; which claims the benefit of priority of French Patent Application No. 0802995 filed Jun. 2, 2008.

The invention relates to a novel salt of 4-bromophenyl 1,4-diazabicyclo[3.2.2]nonane-4-carboxylate, to its crystalline forms, to their preparation and to their therapeutic use.

4-Bromophenyl 1,4-diazabicyclo[3.2.2]nonane-4-carboxylate in the free base form, of formula (I) below, and a process for its preparation are described in the document WO 00/58311.

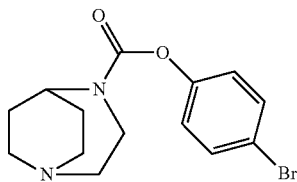

(I)

This compound, among other 1,4-diazabicyclo[3.2.2]nonane-4-carboxylate derivatives, is described as a ligand of the α7 subunits of the nicotinic receptor.

The hydrochloride salt of 4-bromophenyl 1,4-diazabicyclo[3.2.2]nonane-4-carboxylate has furthermore been mentioned in the literature, for example in Pichat P. et al., Neuropsychopharmacology (2007), 32(1), 17-34.

It has now been found that the (2E)-but-2-enedioate salified form (also known as fumarate) of this same compound exhibits advantageous properties, which renders it particularly suitable for use thereof as active principle in a medicament.

A subject matter of the invention is thus the fumarate salt of 4-bromophenyl 1,4-diazabicyclo[3.2.2]nonane-4-carboxylate, its preparation and its therapeutic application.

The fumarate salt of 4-bromophenyl 1,4-diazabicyclo[3.2.2]nonane-4-carboxylate is defined by the formula below.

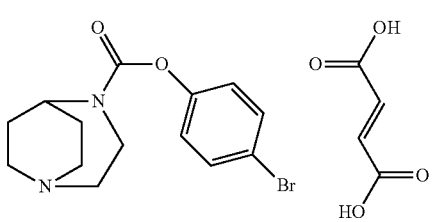 [SMILES: O=C(Oc1ccc(Br)cc1)N1CCN2CCC1CC2 ; O=C(O)/C=C/C(=O)O]

Another subject matter of the invention is the two polymorphic forms of the fumarate salt of 4-bromophenyl 1,4-diazabicyclo[3.2.2]nonane-4-carboxylate, known as form I and form II, the physicochemical characteristics of which are described below.

Characterization of the Form I and of the Form II
Infrared Spectrum

The infrared (I.R.) spectra of the two crystalline forms of the fumarate salt of 4-bromophenyl 1,4-diazabicyclo[3.2.2]nonane-4-carboxylate were recorded on a Fourier-transform spectrophotometer (Nicolet, Magna-IR 550) between 4000 $cm^{-1}$ and 400 $cm^{-1}$ with a resolution of 4 $cm^{-1}$. The compounds, mixed with KBr (at approximately 1% of product w/w), were pelletized and examined in transmission mode.

These spectra are characterized by the absorption bands given in the tables below.

TABLE

| I.R. spectrum, form I |
| $\lambda$ $(cm^{-1})$ |
| --- |
| 2953 |
| 2789 |
| 1735 |
| 1613 |
| 1488 |
| 624 |

TABLE

| I.R. spectrum, form II |
| $\lambda$ $(cm^{-1})$ |
| --- |
| 2952 |
| 1721 |
| 1484 |
| 1200 |
| 638 |

X-Ray Diffractogram

The powder X-ray diffractograms were recorded starting from the powder samples of the form I and the form II.

The analyses were carried out on the D8 Advance diffractometer (Bruker-Siemens), equipped with an Anton-Paar TTK temperature chamber, exhibiting a set-up in reflection, possessing focusing geometry of Bragg-Brentano type (θ-θ).

A copper anticathode tube provides the incident radiation ($\lambda K\alpha 1 = 1.5406$ angströms).

The recording of the diagrams at ambient temperature takes place at from 2 to 40 degrees in 2θ.

Characteristic Lines of the Diffractogram of the Form I

| X-ray diffraction of the form I | |
| --- | --- |
| Peak Angström | Angle 2-theta° |
| d = 20.46 | 4.3 |
| d = 10.26 | 8.6 |
| d = 6.85 | 12.9 |
| d = 4.70 | 18.9 |
| d = 4.47 | 19.8 |
| d = 3.52 | 25.2 |

Characteristic Lines of the Diffractogram of the Form II

| X-ray diffraction of the form II | |
| --- | --- |
| Peak Angström | Angle 2-theta° |
| d = 14.76 | 6.0 |
| d = 9.54 | 9.3 |
| d = 8.75 | 10.1 |
| d = 4.75 | 18.7 |
| d = 3.79 | 23.5 |
| d = 3.69 | 24.1 |

Unit Cell Parameters of the Form I

| Crystallographic data and establishment of the structure of the form I | |
| --- | --- |
| Crystal system Space group | Monoclinic P21/c |
| Dimensions of the unit cell | |
| a | 22.7305 Å |
| b | 7.0571 Å |
| c | 12.7756 Å |
| α | 90° |
| β | 115.207° |
| γ | 90° |
| Volume | 1854.21 |
| Density | 1.57714 |
| Number of molecules per unit cell: Z | 4 |

Unit Cell Parameters of the Form II

| Crystallographic data and establishment of the structure of the form II | |
| --- | --- |
| Crystal system Space group | Monoclinic P21/c |
| Dimensions of the unit cell | |
| a | 16.4735 Å |
| b | 6.4183 Å |
| c | 19.4726 Å |
| α | 90° |
| β | 115.397° |
| γ | 90° |
| Volume | 1859.92 |
| Density | 1.57230 |
| Number of molecules per unit cell: Z | 4 |

Thermogram

Differential calorimetry measurements as a function of the temperature are carried out on the Q1000 thermal analyzer from TA Instruments while flushing with nitrogen. The samples to be analyzed were subjected to a temperature program of 10° C./min from 10 to 350° C. while continually flushing with nitrogen. The powder is placed in crimped and pierced aluminum pans. The amount of product analyzed is approximately 2 mg.

The differential thermodynamic analysis carried out on each polymorph did not exhibit any thermal event before melting.

Summarizing Table for the Thermodynamic Data

|  | Form I | Form II |
| --- | --- | --- |
| Melting point (° C.) +/− 2° C. | 176 | 175 |
| Mean enthalpy (J/g) +/− 2 J/g | 107 | 109 |

Another subject matter of the invention is a process for the preparation of the fumarate salt of 4-bromophenyl 1,4-diazabicyclo[3.2.2]nonane-4-carboxylate and of its crystalline forms.

In accordance with the invention, the compound of general formula (I) can be prepared according to the process described in application WO 00/58311.

The fumarate salt of 4-bromophenyl 1,4-diazabicyclo[3.2.2]nonane-4-carboxylate, form I, can be obtained by reaction of 4-bromophenyl 1,4-diazabicyclo[3.2.2]nonane-4-carboxylate in the base form with fumaric acid in a solvent, such as methanol or ethanol.

The fumarate salt of 4-bromophenyl 1,4-diazabicyclo[3.2.2]nonane-4-carboxylate, form II, can be obtained from the fumarate salt of 4-bromophenyl 1,4-diazabicyclo-[3.2.2]nonane-4-carboxylate, form I, in the presence of an additive (fumarate salt of 2,4-dibromophenyl 1,4-diazabicyclo[3.2.2]nonane-4-carboxylate) in a solvent, such as methanol.

2,4-Dibromophenyl 1,4-diazabicyclo[3.2.2]nonane-4-carboxylate can be obtained according to the process described in the document WO 00/58311 from 2,4-dibromophenyl chloroformate (US2007/0270373). The fumarate salt of 2,4-dibromophenyl 1,4-diazabicyclo[3.2.2]nonane-4-carboxylate can subsequently be formed in the presence of fumaric acid in a solvent, such as methanol or ethanol.

In order to obtain the fumarate salt of 4-bromophenyl 1,4-diazabicyclo[3.2.2]nonane-4-carboxylate, form II, of very good purity, the fumarate salt of 4-bromophenyl 1,4-diazabicyclo[3.2.2]nonane-4-carboxylate, form I, can also be seeded with fumarate salt of 4-bromophenyl 1,4-diazabicyclo[3.2.2]nonane-4-carboxylate, form II, in a solvent, such as methanol.

Examples of the preparation of the fumarate salt of 4-bromophenyl 1,4-diazabicyclo-[3.2.2]nonane-4-carboxylate and of its crystalline forms are described below.

In that which follows, the starting materials and the reactants, when their preparation is not described, are available commercially or are described in the literature or else can be prepared according to methods which are described therein or which are known to a person skilled in the art.

EXAMPLE 1

Preparation of the form I of the fumarate salt of 4-bromophenyl 1,4-diazabicyclo[3.2.2]nonane-4-carboxylate 232.45 g of 4-bromophenyl 1,4-diazabicyclo[3.2.2]nonane-4-carboxylate (WO 00/58311) are placed in 2331 ml of ethanol in a 6 l jacketed reactor. The reaction medium is brought to 60° C. A solution of 87.17 g of fumaric acid in 1000 ml of ethanol and 97 ml of water, heated beforehand to 60° C., is then added. 1900 ml of solvent are subsequently distilled off and then the reaction medium is cooled to 20° C. over 2.5 h. After a contact time of 2.5 h at 20° C., the form I of the fumarate salt of 4-bromophenyl 1,4-diazabicyclo [3.2.2]nonane-4-carboxylate is filtered off, washed with 2 times 400 ml of ethanol and then dried under vacuum at 50° C.

Melting point (DSC): 175° C.
$^1$H NMR (400 MHz, $d_6$-DMSO) δ (ppm): 1.80 (bs$^{(a)}$, 2H), 2.10 (bs, 2H), 3.10 (bs, 6H), 3.71 (bs, 1H), 3.84 (bs, 1H), 4.25 (bs, 0.5H), 4.40 (bs, 0.5H), 6.58 (s, 2H), 7.14 (m, 2H), 7.57 (m, 2H), 11 (bs, 2H).
$^{(a)}$bs=broad singlet.

EXAMPLE 2

Preparation of the form I of the fumarate salt of 4-bromophenyl 1,4-diazabicyclo[3.2.2]nonane-4-carboxylate 24.26 kg of 4-bromophenyl 1,4-diazabicyclo[3.2.2] nonane-4-carboxylate and 8.52 kg (1.1 eq.) of fumaric acid are placed in 197 l of methanol in a 630 l jacketed enameled reactor. The reaction medium is stirred at 65° C. until completely dissolved. The latter is cooled to 45° C. over 2 h and then initiated with 0.5% of form I of the fumarate salt of 4-bromophenyl 1,4-diazabicyclo[3.2.2]nonane-4-carboxylate. The temperature is maintained for one hour. The reaction medium is subsequently cooled to 0° C. over 4.5 h and then maintained at this temperature for 2 h. The form I of the fumarate salt of 4-bromophenyl 1,4-diazabicyclo[3.2.2] nonane-4-carboxylate is filtered off, washed with 2 times 24 l of cold methanol and then dried under vacuum at 60° C.

Melting point (DSC): 175° C.

$^1$H NMR (400 MHz, d$_6$-DMSO) δ (ppm): 1.80 (bs$^{(a)}$, 2H), 2.10 (bs, 2H), 3.10 (bs, 6H), 3.71 (bs, 1H), 3.84 (bs, 1H), 4.25 (bs, 0.5H), 4.40 (bs, 0.5H), 6.58 (s, 2H), 7.14 (m, 2H), 7.57 (m, 2H), 11 (bs, 2H).

$^{(a)}$bs=broad singlet.

EXAMPLE 3

Preparation of the form II of the fumarate salt of 4-bromophenyl 1,4-diazabicyclo[3.2.2]nonane-4-carboxylate A) Crystallization of the Form II by Addition of Additive A solution A of fumarate salt of 4-bromophenyl 1,4-diazabicyclo[3.2.2]nonane-4-carboxylate, form I, in methanol with a concentration approximately equal to 30 mg/ml is prepared. If necessary, heating is carried out to approximately 40° C. in order to dissolve all of the product, and then filtration is carried out.

A solution B of additive in methanol with a concentration approximately equal to 3 mg/ml is prepared. The additive is the fumarate salt of 2,4-dibromophenyl 1,4-diazabicyclo [3.2.2]nonane-4-carboxylate.

The solution B and the solution A are mixed in order to obtain a solution C with an additive/4-bromophenyl 1,4-diazabicyclo[3.2.2]nonane-4-carboxylate, form I, ratio approximately equal to 0.003.

2 ml of solution C are evaporated in a beaker with magnetic stirring at ambient temperature for approximately 24 h. Several beakers corresponding to several tests can optionally be prepared.

The product D obtained after evaporation is analyzed by powder diffraction in order to confirm that it is the form II of the fumarate salt of 4-bromophenyl 1,4-diazabicyclo-[3.2.2] nonane-4-carboxylate.

B) Purification

A solution E of fumarate salt of 4-bromophenyl 1,4-diazabicyclo[3.2.2]nonane-4-carboxylate, form I, in methanol with a concentration approximately equal to 100 mg/ml is prepared. The solution is heated at reflux for approximately 15 min and then filtered. The temperature of the solution E is lowered to approximately 10° C.

Approximately 0.5% by weight of product D (form II prepared in stage A), with respect to the amount of fumarate salt of 4-bromophenyl 1,4-diazabicyclo[3.2.2]nonane-4-carboxylate, form I, present in the solution E, is added. The mixture is stirred at approximately −10° C. for approximately 2 h.

The product F obtained is filtered off and then dried while flushing with dry nitrogen. An analysis is carried out by powder X-ray diffraction in order to confirm that it is the form II of the fumarate salt of 4-bromophenyl 1,4-diazabicyclo [3.2.2]nonane-4-carboxylate.

If it is desired to further improve the purity of the fumarate salt of 4-bromophenyl 1,4-diazabicyclo[3.2.2]nonane-4-carboxylate, form II, stage B can optionally be repeated while seeding with the product F instead of the product D.

Unexpectedly, it has specifically been demonstrated that the fumarate salt of the compound of formula (I) has properties of purity, of stability and of solubility which are further improved with respect to the same compound in the base form.

This is because it is very difficult to purify the compound of formula (I) in the base form. The salification stage, that is to say the change from 4-bromophenyl 1,4-diazabicyclo[3.2.2] nonane-4-carboxylate in the free base form to the fumarate salt, is a stage which makes it possible to chemically purify the compound, as is shown by the results for quantitative determination of the impurities by HPLC (High Performance Liquid Chromatography) presented below (table 1).

Chromatographic Conditions

Column: Inertsil ODS 3 150×4.6 mm, 5 μm, maintained at 25° C.

Mobile phase:

Buffer pH 4.5: 0.01M KH$_2$PO$_4$, 0.5 g/l sodium heptanesulfonate pH adjusted to 4.5 with 1M KOH Phase A: 90 V buffer pH 4.5
10 V acetonitrile Phase B: 20 V buffer pH 4.5
80 V acetonitrile Gradient: from 100% of phase A to 80% of phase B in 40 min Flow rate: 1.0 ml/min Detection: UV, λ=220 nm (optical path: 1 cm)

Solutions injected: 0.2 mg (base or salt)/ml solutions in a mixture of 50 volumes of water and 50 volumes of acetonitrile.

Comment: for the quantitative determinations, the results obtained are expressed in % (w/w) of nondecomposed base (by calibrating with nondecomposed base or salt controls stored at ambient temperature).

TABLE 1

| Purity of the samples | | |
|---|---|---|
|  | Base | Fumarate |
| Purity by HPLC | 95.5 | 100 |

The fumarate salt was obtained with a satisfactory purity, in contrast to the base, which exhibits a purity of 95.5%.

Furthermore, the fumarate salt of 4-bromophenyl 1,4-diazabicyclo[3.2.2]nonane-4-carboxylate is more stable than 4-bromophenyl 1,4-diazabicyclo[3.2.2]nonane-4-carboxylate in the free base form. This is because the melting point of 4-bromophenyl 1,4-diazabicyclo[3.2.2]nonane-4-carboxylate in the free base form is 112° C. and its enthalpy of fusion is 29 kJ/mol, while the melting point of the fumarate salt of 4-bromophenyl 1,4-diazabicyclo[3.2.2]nonane-4-carboxylate is 175-176° C. (respectively form II-form I) and the enthalpy of fusion is 39 kJ/mol.

Test of thermal stability in the solid state

The base and the fumarate salt of the compound of formula (I) are analyzed after 1, 7 and 14 days of storage at:

80° C.;

80° C. and under 80% relative humidity (RH).

Appearance

The results are described in table 2 below.

TABLE 2

Appearance - Results after 1, 7 and 14 d at 80° C. and 80° C./80% RH

| Conditions | Duration | Base | Fumarate |
|---|---|---|---|
| Initial appearance | — | Virtually white powder | White powder |
| 80° C. | 1 d | Pale yellow | unchanged |
| | 7 d | Pale yellow | unchanged |
| | 14 d | Pale yellow | unchanged |
| 80° C./80% RH | 1 d | Yellow-brown | unchanged |
| | 7 d | Brown | unchanged |
| | 14 d | Brown | unchanged |

In the light of the results obtained above, it is found that the base of the compound of formula (I) changes in appearance under the effect of heat and under the effect of heat and humidity, which reflects a deterioration in the chemical quality of the product. In contrast, the appearance of the fumarate salt of the compound of formula (I) remains unchanged. These results thus demonstrate a greater stability of the fumarate salt with respect to the base of the compound of formula (I) under the conditions tested.

Quantitative Determination of the Nondecomposed Product and Percentage of Impurities Chromatographic Conditions Column: Inertsil ODS 3 150×4.6 mm, 5 μm, maintained at 25° C.

Mobile phase:

Buffer pH 4.5: 0.01M $KH_2PO_4$, 0.5 g/l sodium heptanesulfonate pH adjusted to 4.5 with 1M KOH Phase A: 90 V buffer pH 4.5
10 V acetonitrile Phase B: 20 V buffer pH 4.5
80 V acetonitrile Gradient: from 100% of phase A to 80% of phase B in 40 min Flow rate: 1.0 ml/min Detection: UV, λ=220 nm (optical path: 1 cm)

Solutions injected: 0.2 mg (base or salt)/ml solutions in a mixture of 50 volumes of water and 50 volumes of acetonitrile.

Comment: for the quantitative determinations, the results obtained are expressed in % (w/w) of nondecomposed base (by calibrating with nondecomposed base or salt controls stored at ambient temperature).

The results of quantitative determination by HPLC are summarized in table 3 below.

TABLE 3

| | | Base | | Fumarate | |
|---|---|---|---|---|---|
| Conditions | Duration | Non-decomposed base (%) | Sum % imp. quantified (% surf.) | Non-decomposed product (%) | Sum % imp. quantified (% surf.) |
| Initial | — | — | 4.02 | — | 0.32 |
| 80° C. | 7 d | 100 | 3.57 | 99.6 | 0.60 |
| | 14 d | 99.9 | 3.14 | 100 | 0.53 |
| 80° C./ 80% RH | 7 d | 98.7 | 4.37 | 99.7 | 0.74 |
| | 14 d | 98.3 | 4.53 | 100 | 0.83 |

The fumarate salt thus decomposes less than the base toward heat and toward heat in the presence of humidity. Comment: the sum of the impurities quantified may be less after storing at 80° C. under 80% relative humidity because impurities may decompose to give products which cannot be detected by UV or which are not separated by the analytical conditions.

Furthermore, within a pharmaceutical formulation, the fumarate salt of 4-bromophenyl 1,4-diazabicyclo[3.2.2]nonane-4-carboxylate is less reactive with regard to the excipients than 4-bromophenyl 1,4-diazabicyclo[3.2.2]nonane-4-carboxylate in the free base form. This is because, in the case of the fumarate salt, the ionic bond between the fumaric acid and the 4-bromophenyl 1,4-diazabicyclo[3.2.2]nonane-4-carboxylate is formed at the secondary amine. In the case of the free base, the absence of a bond results in a greater reactivity with the excipients during the formulation.

Finally, the fumarate salt of 4-bromophenyl 1,4-diazabicyclo[3.2.2]nonane-4-carboxylate is more soluble than 4-bromophenyl 1,4-diazabicyclo[3.2.2]nonane-4-carboxylate in the free base form, as is shown by the analyses described below.

Solubility Tests

The instantaneous solubilities of the base and of the fumarate salt of the compound of formula (I) were determined in the following media:

water;

buffer pH 1.2: 0.01M $KH_2PO_4$, pH adjusted with orthophosphoric acid;

buffer pH 7.2: 0.2M $KH_2PO_4$, pH adjusted with KOH;

buffer pH 9.0: 0.04M $Na_2B_4O_7.10H_2O$, pH adjusted with boric acid;

dimethyl sulfoxide (DMSO).

Determination of the instantaneous solubilities: successive volumes of the medium are added to the test specimen until the compound has dissolved. Stirring is carried out with a vortex mixer at ambient temperature.

The results are described in table 4 below. Information on the corresponding classification according to the European Pharmacopoeia is also given therein.

TABLE 4

Instantaneous solubilities of the base and of the fumarate salt of the compound of formula (I) and corresponding classification according to the European Pharmacopoeia
(in g of product/l)

| Medium | Base | | Fumarate | |
|---|---|---|---|---|
| Water | <2 | Slightly soluble | ~27 | Sparingly soluble |
| pH 1.2 | 140 | Freely soluble | ~16 | Sparingly soluble |
| pH 7.2 | <2 | Slightly soluble | ~75 | Soluble |
| pH 9.0 | <2 | Slightly soluble | ~68 | Soluble |
| DMSO | ~75 | Soluble | ~140 | Freely soluble |

In the light of the results of table 4, it is found that the fumarate salt of the compound of formula (I) is overall more soluble than the compound of formula (I) in the free base form.

It has also been demonstrated that the fumarate form of the compound of formula (I) has improved properties of temperature stability in comparison with the hydrochloride form of the same compound.

This is because, under the effect of temperature or when flushing with nitrogen, the hydrochloride salt of 4-bromophenyl 1,4-diazabicyclo[3.2.2]nonane-4-carboxylate has a tendency to lose its water stoichiometry. Thus, the monitoring and the control of the crystalline phase, during the drying stage after the salification stage and during the formulation stage, in the case of a pharmaceutical formulation of the compound, exhibit numerous constraints. The water sorption/desorption isotherm shows that the hydrochloride of the compound A is present in a hemihydrate form and two anhydrous forms; this water content, which is difficult to control, increases the sensitivity to drying and makes it difficult to use the hydrochloride on an industrial scale.

In contrast, the fumarate salt of 4-bromophenyl 1,4-diazabicyclo[3.2.2]nonane-4-carboxylate crystallizes in two nonhygroscopic polymorphic forms (forms I and II). The presence of water in the vapor or liquid form has no impact on the crystalline form of the form I or of the form II of the fumarate salt of 4-bromophenyl 1,4-diazabicyclo[3.2.2]nonane-4-carboxylate. This property of the two polymorphic forms of the fumarate salt of 4-bromophenyl 1,4-diazabicyclo[3.2.2]nonane-4-carboxylate is an advantage in comparison with the hydrochloride salt of 4-bromophenyl 1,4-diazabicyclo[3.2.2]nonane-4-carboxylate.

It emerges from these analyses that the fumarate salt of the compound of formula (I) simultaneously exhibits better properties of solubility and of stability than those of the compound of formula (I) in the base form or hydrochloride salt form which renders it particularly suitable for the manufacture of medicaments.

The physicochemical properties of the compound of formula (I) in the fumarate salt form also allow it to be stored under normal conditions without excessively restrictive precautions with respect to the presence of light, the temperature and the humidity.

The fumarate salt of 4-bromophenyl 1,4-diazabicyclo[3.2.2]nonane-4-carboxylate is a ligand of the $\alpha 7$ subunits of the nicotinic receptor.

As such, it can be used in the preparation of medicaments, in particular of medicaments intended to treat or to prevent disorders related to a dysfunctioning of the nicotinic receptors, in particular in the central nervous system but also in the peripheral system.

These disorders comprise detrimental cognitive changes, more specifically detrimental memory changes (acquisition, consolidation and recall), but also attacks on attentional processes, and disorders of the executive functions related to Alzheimer's disease, to pathological ageing (age associated memory impairment, AAMI) or normal ageing (senile dementia), to Parkinsonian syndrome, to trisomy 21 (Down's syndrome), to psychiatric pathologies, in particular cognitive impairment associated with schizophrenia (CIAS) or post-traumatic stress disorder (PTSD), to Korsakoff's alcoholic syndrome, to vascular dementias (multiinfarct dementia, MDI) or to cranial traumas.

The compound of the invention might also be of use in the treatment of motor disorders observed in Parkinson's disease or other neurological diseases, such as Huntington's chorea, Tourette's syndrome, tardive dyskinesia and hyperkinesia.

It might also exhibit a neuroprotective therapeutic activity with respect to anatomic histopathological attacks related to the abovementioned neurodegenerative diseases.

It might also be of use in the treatment of multiple sclerosis.

The compound of the invention might also constitute a curative or symptomatic treatment of strokes and cerebral hypoxic episodes. It can be used in the case of psychiatric pathologies: schizophrenia (positive and/or negative symptoms), bipolar disorders, depression, anxiety, panic attacks, PTSD, attention deficit hyperactivity disorder (ADHD) or obsessive-compulsive behavior.

It might prevent symptoms due to weaning from tobacco, from alcohol or from various dependence-inducing substances, such as cocaine, LSD, cannabis or benzodiazepines.

It might be of use in the treatment of pain of various origins (including chronic, neuropathic or inflammatory pain).

Furthermore, the compound of the invention might be used in the treatment of lower limb ischemia, lower limb arterial occlusive disease (PAD: peripheral arterial disease), cardiac ischemia (stable angina), myocardial infarction, cardiac insufficiency, skin healing deficiency in diabetic patients, varicose ulcers of venous insufficiency, or septic shock.

The compound of the invention might also be used in the treatment of inflammatory processes of various origins, in particular inflammation relating to the central nervous system, pulmonary inflammation related to allergies or to asthma, periodontitis, sarcoidosis, pancreatitis, reperfusion injuries or rheumatoid arthritis.

The compound of the invention might also be of use in the treatment of dermatological pathologies, such as psoriasis, and in the treatment of asthma.

The compound of the invention might also be used in the treatment of ulcerative colitis.

Thus, according to another of its aspects, a subject matter of the invention is medicaments which comprise the fumarate salt of 4-bromophenyl 1,4-diazabicyclo-[3.2.2]nonane-4-carboxylate. These medicaments are employed therapeutically, in particular in the treatment and prevention of disorders related to a dysfunctioning of the nicotinic receptors, in particular the abovementioned disorders.

Another subject matter of the invention is thus the use of the fumarate salt of 4-bromophenyl 1,4-diazabicyclo[3.2.2]nonane-4-carboxylate in the preparation of a medicament intended to treat or to prevent disorders related to a dysfunctioning of the nicotinic receptors, in particular the abovementioned disorders.

According to another of its aspects, the present invention relates to pharmaceutical compositions comprising, as active principle, the fumarate salt of 4-bromophenyl 1,4-diazabicyclo[3.2.2]nonane-4-carboxylate. These pharmaceutical compositions comprise an effective dose of the fumarate salt of 4-bromophenyl 1,4-diazabicyclo-[3.2.2]nonane-4-carboxylate, and also at least one pharmaceutically acceptable excipient. Said excipients are chosen, according to the pharmaceutical form desired and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the fumarate salt of 4-bromophenyl 1,4-diazabicyclo[3.2.2]nonane-4-carboxylate can be administered in unit administration form, as a mixture with conventional pharmaceutical excipients, to animals and human beings for the prophylaxis or treatment of the above disorders or diseases.

The appropriate unit administration forms comprise the forms by the oral route, such as tablets, soft or hard gelatin capsules, powders, granules and solutions or suspensions to be taken orally, the forms for sublingual, buccal, intratracheal, intraocular or intranasal administration, the forms for administration by inhalation, the forms for topical, transdermal, subcutaneous, intramuscular or intravenous administration, the forms for rectal administration and implants. Use may be made, for topical application, of the compound according to the invention in creams, gels, ointments or lotions.

Said unit forms comprise a dose in order to make possible daily administration of 0.01 to 20 mg of active principle per kg of body weight, depending on the pharmaceutical formulation form.

There may be specific cases where higher or lower dosages are appropriate; such dosages do not depart from the scope of the invention. According to the usual practice, the dosage appropriate to each patient is determined by the physician according to the method of administration and the weight and the response of said patient.

The present invention, according to another of its aspects, also relates to a method for the treatment of the pathologies indicated above which comprises the administration, to a patient, of an effective dose of fumarate salt of 4-bromophenyl 1,4-diazabicyclo[3.2.2]nonane-4-carboxylate.

What is claimed is:

1. A fumarate salt of 4-bromophenyl 1,4-diazabicyclo-[3.2.2]nonane-4-carboxylate, selected from the group consisting of the crystalline polymorphic form I and the crystalline polymorphic form II.

2. The fumarate salt of 4-bromophenyl 1,4-diazabicyclo [3.2.2]nonane-4-carboxylate according to claim 1, wherein it is in the crystalline polymorphic form I.

3. The fumarate salt of 4-bromophenyl 1,4-diazabicyclo [3.2.2]nonane-4-carboxylate according to claim 2, the infrared spectrum of which exhibits at least three of the following characteristic absorption bands:

| $\lambda$ (cm$^{-1}$) |
|---|
| 2953 |
| 2789 |
| 1735 |
| 1613 |
| 1488 |
| 624. |

4. The fumarate salt of 4-bromophenyl 1,4-diazabicyclo [3.2.2]nonane-4-carboxylate according to claim 2, the powder X-ray diffractogram of which comprises at least three of the following characteristic lines:

| Peak Angström | Angle 2-theta° |
|---|---|
| d = 20.46 | 4.3 |
| d = 10.26 | 8.6 |
| d = 6.85 | 12.9 |
| d = 4.70 | 18.9 |
| d = 4.47 | 19.8 |
| d = 3.52 | 25.2. |

5. The fumarate salt of 4-bromophenyl 1,4-diazabicyclo [3.2.2]nonane-4-carboxylate according to claim 2 having a melting point of 176° C.+/−2° C. and a mean enthalpy of 107 J/g+/−2 J/g.

6. The fumarate salt of 4-bromophenyl 1,4-diazabicyclo [3.2.2]nonane-4-carboxylate according to claim 1, wherein it is in the crystalline polymorphic form II.

7. The fumarate salt of 4-bromophenyl 1,4-diazabicyclo [3.2.2]nonane-4-carboxylate according to claim 6, the infrared spectrum of which exhibits at least three of the following characteristic absorption bands:

| $\lambda$ (cm$^{-1}$) |
|---|
| 2952 |
| 1721 |
| 1484 |
| 1200 |
| 638. |

8. The fumarate salt of 4-bromophenyl 1,4-diazabicyclo [3.2.2]nonane-4-carboxylate according to claim 6, the powder X-ray diffractogram of which comprises at least three of the following characteristic lines:

| Peak Angström | Angle 2-theta° |
|---|---|
| d = 14.76 | 6.0 |
| d = 9.54 | 9.3 |
| d = 8.75 | 10.1 |
| d = 4.75 | 18.7 |
| d = 3.79 | 23.5 |
| d = 3.69 | 24.1. |

9. The fumarate salt of 4-bromophenyl 1,4-diazabicyclo [3.2.2]nonane-4-carboxylate according to claim 6, having a melting point of 175° C.+/−2° C. and a mean enthalpy of 109 J/g+/−2 J/g.

10. A process for the preparation of the fumarate salt of 4-bromophenyl 1,4-diazabicyclo[3.2.2]nonane-4-carboxylate, form I, according to claim 2, comprising reacting 4-bromophenyl 1,4-diazabicyclo[3.2.2]nonane-4-carboxylate in the free base form with fumaric acid in a solvent.

11. A process for the preparation of the fumarate salt of 4-bromophenyl 1,4-diazabicyclo[3.2.2]nonane-4-carboxylate, form II, according to claim 6, comprising bringing the fumarate salt of 4-bromophenyl 1,4-diazabicyclo[3.2.2] nonane-4-carboxylate, form I, together with the fumarate salt of 2,4-dibromophenyl 1,4-diazabicyclo[3.2.2]nonane-4-carboxylate in a solvent.

12. A pharmaceutical composition comprising, as active principle, the fumarate salt of 4-bromophenyl 1,4-diazabicyclo[3.2.2]nonane-4-carboxylate according to claim 1, and at least one pharmaceutically acceptable excipient.

13. A method of treating a disorder related to a dysfunctioning of the nicotinic receptors in a patient comprising administering to the patient an effective dose of the fumarate salt of 4-bromophenyl 1,4-diazabicyclo[3.2.2]nonane-4-carboxylate according to claim 1; wherein said disorder is selected from the group consisting of detrimental memory changes, disorder of the executive functions related to Alzheimer's disease, age associated memory impairment, senile dementia, Parkinsonian syndrome, trisomy 21, cognitive impairment associated with schizophrenia or post-traumatic stress disorder, Korsakoff's alcoholic syndrome, vascular dementia, cranial trauma, motor disorders observed in Parkinson's disease; multiple sclerosis, stroke, cerebral hypoxic episode, positive and/or negative symptoms of schizophrenia, bipolar disorder, depression, anxiety, panic attacks, attention deficit hyperactivity disorder, obsessive-compulsive behavior, symptoms due to weaning from dependence-inducing substances, pain, lower limb ischemia, lower limb arterial occlusive disease, cardiac ischemia, myocardial infarction, cardiac insufficiency, skin healing deficiency in diabetic patients, varicose ulcers of venous insufficiency, septic shock, inflammation, psoriasis, asthma, and ulcerative colitis.

14. The method according to claim 13 wherein the disorder is a disorder of the executive functions related to Alzheimer's disease.

15. The method according to claim 13 wherein the disorder is cognitive impairment associated with schizophrenia.

* * * * *